United States Patent
Nakata et al.

(10) Patent No.: US 9,414,795 B2
(45) Date of Patent: Aug. 16, 2016

(54) RADIATION GENERATING APPARATUS AND RADIATION IMAGING APPARATUS

(71) Applicant: CANON KABUSHIKI KAISHA, Tokyo (JP)

(72) Inventors: Takeshi Nakata, Kawasaki (JP); Hideki Hayashi, Kiyose (JP); Hitomi Ogasawara, Kawasaki (JP); Kenta Koyama, Tokyo (JP); Kazuhiro Watanabe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 66 days.

(21) Appl. No.: 14/483,018

(22) Filed: Sep. 10, 2014

(65) Prior Publication Data

US 2015/0069256 A1 Mar. 12, 2015

(30) Foreign Application Priority Data

Sep. 12, 2013 (JP) ................................. 2013-189448

(51) Int. Cl.
*A61B 6/00* (2006.01)

(52) U.S. Cl.
CPC ............. *A61B 6/4405* (2013.01); *A61B 6/4411* (2013.01); *A61B 6/4429* (2013.01)

(58) Field of Classification Search
CPC ...... A61B 6/44; A61B 6/4405; A61B 6/4411; A61B 6/4429; A61B 6/4435
USPC ........................................... 378/62, 196–198
See application file for complete search history.

(56) References Cited

U.S. PATENT DOCUMENTS

| | | | | |
|---|---|---|---|---|
| 6,754,306 B2* | 6/2004 | Cho | ........................ | G01N 23/04 378/102 |
| 6,851,853 B2* | 2/2005 | Nakagawa | ............ | A61B 6/4405 378/197 |
| 6,863,439 B2* | 3/2005 | Morris | ...................... | A61B 6/04 378/192 |
| 6,999,558 B2* | 2/2006 | Okoda | ................. | A61B 6/4233 378/102 |
| 7,023,959 B2* | 4/2006 | Nakagawa | ............ | A61B 6/4405 378/98 |
| 7,309,159 B2* | 12/2007 | Watanabe | ............ | A61B 6/4405 378/117 |
| 7,438,470 B2* | 10/2008 | Koren | ....................... | A61B 6/00 378/198 |
| 7,611,282 B2* | 11/2009 | Koren | ................... | A61B 6/4233 378/198 |
| 7,744,279 B2* | 6/2010 | Heath | ....................... | A61B 6/08 378/196 |
| 8,357,904 B2* | 1/2013 | Tsuchiya | ................ | A61B 6/037 250/363.02 |
| 8,376,612 B2* | 2/2013 | Takae | .................... | A61B 6/4283 378/198 |
| 8,419,276 B2* | 4/2013 | Oda | ....................... | A61B 6/4405 378/198 |
| 8,705,699 B2* | 4/2014 | Fuse | ..................... | A61B 6/4405 378/102 |
| 8,929,510 B2* | 1/2015 | Nishino | ............... | A61B 6/4216 378/102 |
| 8,961,011 B2* | 2/2015 | Lalena | .................. | A61B 6/4405 378/197 |
| 8,976,931 B2* | 3/2015 | Lalena | .................. | A61B 6/4405 378/98.5 |
| 9,055,911 B2* | 6/2015 | Sakuragi | ............... | A61B 6/4429 |
| 9,060,741 B2* | 6/2015 | Fuse | ..................... | A61B 6/4405 |
| 9,078,597 B2* | 7/2015 | Patil | ........................ | A61B 6/107 |
| 9,101,319 B2* | 8/2015 | Kojima | ................. | A61B 6/4405 |
| 9,121,805 B2* | 9/2015 | Omura | ................. | A61B 6/4405 |
| 9,125,611 B2* | 9/2015 | Eaves | ................... | A61B 6/4405 |
| 9,282,940 B2* | 3/2016 | Nishimura | ........... | A61B 6/4405 |
| 2007/0133753 A1* | 6/2007 | Jakob | ................... | A61B 6/4405 378/198 |
| 2014/0093045 A1* | 4/2014 | Shimada | .................. | A61B 6/44 378/98 |
| 2014/0098942 A1* | 4/2014 | Omura | ................. | A61B 6/4405 378/197 |
| 2014/0233705 A1* | 8/2014 | Kaku | .................... | A61B 6/4405 378/117 |
| 2014/0291540 A1* | 10/2014 | Sakuragi | ............... | A61B 6/4405 250/393 |
| 2014/0291555 A1* | 10/2014 | Sakuragi | ............... | A61B 6/4429 250/493.1 |

FOREIGN PATENT DOCUMENTS

JP 2007-144161 A 6/2007

* cited by examiner

*Primary Examiner* — Allen C. Ho
(74) *Attorney, Agent, or Firm* — Canon USA Inc., IP Division

(57) ABSTRACT

There are provided a radiation generating apparatus and a radiation imaging apparatus that have excellent transportability. The radiation generating apparatus and radiation imaging apparatus include a radiation generating unit configured to generate radiation, an arm configured to support the radiation generating unit, and a support pillar configured to support the arm and rotate the arm, wherein the support pillar has a housing portion that has a space for housing at least a part of the radiation generating unit.

12 Claims, 5 Drawing Sheets

FIG. 4A
FIG. 4B
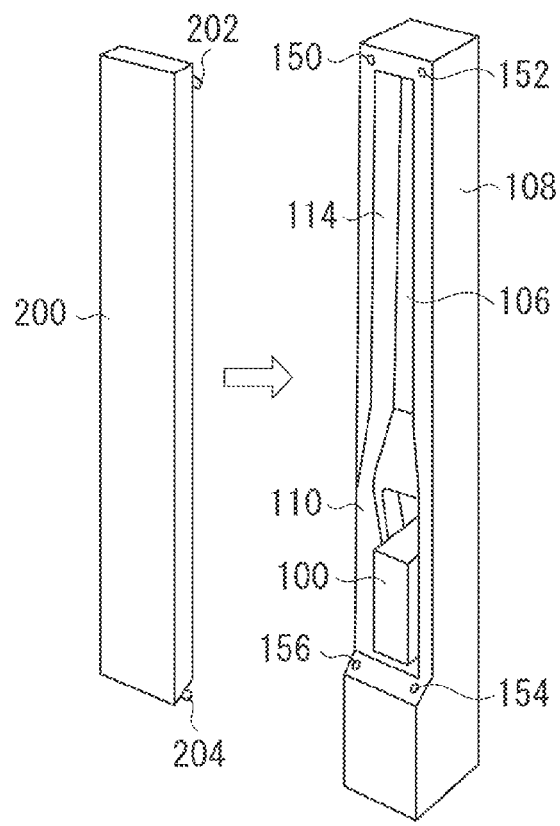
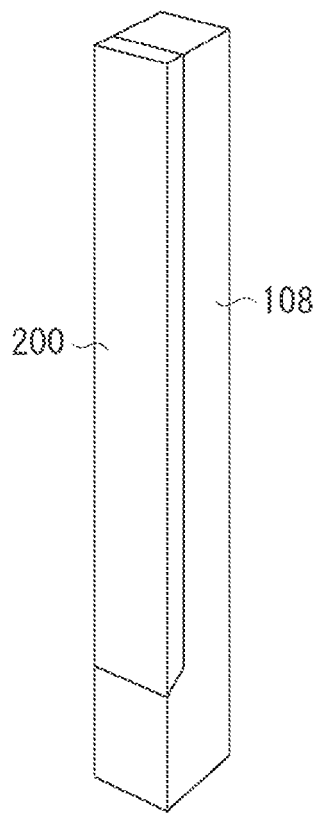

RADIATION GENERATING APPARATUS AND RADIATION IMAGING APPARATUS

BACKGROUND OF THE INVENTION

1. Field of the Invention

The present invention relates to a radiation generating apparatus including a support mechanism that supports a radiation generating unit configured to emit radiation, and a radiation imaging apparatus.

2. Description of the Related Art

Conventionally, a radiation generating apparatus is installed in an X-ray room in a hospital, for example, and used inside that room. Recently, a mobile radiation imaging apparatus that can be easily moved has also been developed, enabling radiation imaging to be carried out by moving the apparatus to a hospital room.

A mobile radiation imaging apparatus has a configuration in which an arm that supports a radiation generating unit and a support pillar that supports the arm by pinching the arm therein (see Japanese Patent Application Laid-Open No. 2007-144161).

However, since the mobile radiation imaging apparatus discussed in Japanese Patent Application Laid-Open No. 2007-144161 includes a cart in which the arm is pinched in the support pillar, transportability is poor. Consequently, there is a need for improvement of the radiation generating apparatus and the radiation imaging apparatus.

SUMMARY OF THE INVENTION

The present invention is directed to a radiation generating apparatus and a radiation imaging apparatus that have excellent transportability.

According to an aspect of the present invention, a radiation generating apparatus includes a radiation generating unit configured to generate radiation, an arm configured to support the radiation generating unit, and a support pillar configured to support the arm and rotate the arm, wherein the support pillar has a housing portion that has a space for housing at least a part of the radiation generating unit.

According to another aspect of the present invention, a radiation imaging apparatus includes the above-described radiation generating apparatus, a radiation detection apparatus configured to detect radiation that has passed through a subject, and a display device configured to display an image generated based on detected data.

Further features of the present invention will become apparent from the following description of exemplary embodiments with reference to the attached drawings.

BRIEF DESCRIPTION OF THE DRAWINGS

FIGS. 4A and 4B illustrate an appearance of a radiation generating apparatus according to a second exemplary embodiment of the present invention.

DESCRIPTION OF THE EMBODIMENTS

Figure 1:
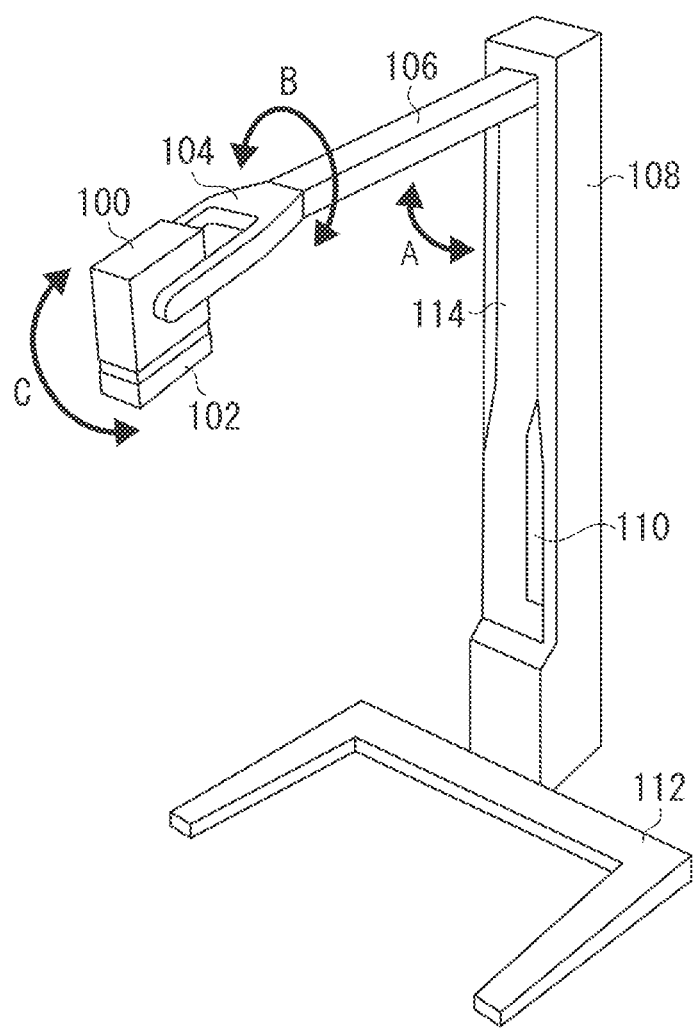
FIG. 1 illustrates an appearance of a radiation generating apparatus according to a first exemplary embodiment of the present invention.

Various exemplary embodiments, features, and aspects of the invention will be described in detail below with reference to the drawings. Further, unless stated otherwise, common or similar parts in the exemplary embodiments are denoted with the same reference numerals, and a duplicate description of such parts is omitted.

FIG. 1 illustrates an appearance of a radiation generating apparatus (radiation imaging apparatus) according to a first exemplary embodiment of the present invention. The radiation generating apparatus includes a support pedestal 112 installed on the floor, a support pillar 108 that stands erect in the vertical direction with respect to the support pedestal 112, an arm 106 that is rotatably arranged with respect to the support pillar 108, and a radiation generating unit 100 that is rotatably arranged with respect to the arm 106 and is configured to emit radiation. To make the radiation generating apparatus as compact as possible, a form in which the radiation generating apparatus does not include a display device for displaying images, is illustrated. Further, the support pillar 108 and the arm 106 can also be depicted as a support mechanism that supports the radiation generating unit 100 which generates radiation.

The radiation generating unit 100, which is configured to generate radiation, includes, for example, a radiation tube that emit radiation and a diaphragm for controlling an irradiation area of the radiation. An aperture portion 102 is an unshielded aperture through which the radiation emitted from the radiation generating unit 100 can pass. Therefore, the aperture direction of the aperture portion 102 becomes the emission direction of the radiation.

The radiation generating unit 100 is a transmission type radiation generating unit. The transmission type radiation generating unit is provided with a radiation shielding member on the target electron incident side and the radiation emission side to shield unnecessary radiation. The transmission type radiation generating unit can be realized in a smaller, lighter configuration than a rotating anode type radiation generating unit, for example, because it is not necessary to cover the whole periphery of the radiation tube or the enclosure housing the radiation tube with a shielding material such as lead.

The arm 106 is an arm that links the radiation generating unit 100 and the support pillar 108. The arm 106, which supports the radiation generating unit 100, has a predetermined length. Further, the arm 106 may include an extension/contraction mechanism for extending/contracting the arm 106 in a longitudinal direction, and a rotation mechanism for rotating the arm 106 with an articulated mechanism that can bend in various directions. By extending the arm 106 in a predetermined direction, the radiation generating unit 100 can be moved toward a subject side.

The arm 106 can be rotated about an upper end of the support pillar 108. More specifically, the support pillar 108 has an arm hinge (not illustrated) for allowing the arm 106 to rotate in a predetermined rotating direction (direction A). For example, the support pillar 108 may have the arm hinge at the upper end of the support pillar 108. The arm 106 has a rotating range of about 90° in the predetermined rotating direction (direction A). Thus, the arm hinge is a mechanism that couples the arm 106 and the support pillar 108, and is capable of opening/closing the arm 106 with respect to the support pillar 108. When the arm 106 is folded, the arm 106 is in a substantially parallel state to the support pillar 108.

Thus, by rotating the arm 106 in a predetermined direction (direction A) via the arm hinge, as illustrated in FIG. 1, the arm 106 can be changed from a form in which the arm 106 is extended in the horizontal direction to a form in which the arm 106 is housed with the radiation generating unit 100. The expression "form in which the arm 106 is extended in the horizontal direction" refers to a state in which the radiation generating unit 100 is moved toward the subject side. The expression "form in which the arm 106 is housed with the radiation generating unit 100" refers to a state in which the arm 106 is folded, and the arm 106 is substantially parallel to the support pillar 108. In other words, it is a state in which the radiation generating unit 100 is arranged near the floor. Further, a specific example of the arm 106 being housed with the radiation generating unit 100 in the support pillar 108 will be described below.

Further, the radiation generating unit 100 is attached to the end of the arm 106. An articulating mechanism 104 that is coupled with the radiation generating unit 100 and rotates the radiation generating unit 100 is provided at the end of the arm 106. The articulating mechanism 104 enables the angle of the radiation generating unit 100 to be varied with respect to a plurality of rotational axes. A resistance derived from a hydraulic mechanism, for example, is applied to the articulating mechanism 104. When the operator applies a certain level of force thereto, the angle of the radiation generating unit 100 changes. Accordingly, the operator can change the angle of the radiation generating unit 100 without wobbling.

As illustrated in FIG. 1, the articulating mechanism 104 enables the radiation generating unit 100 to be moved from side to side and up and down when the arm 106 is in a horizontal state, so that the position of the radiation generating unit 100 can be adjusted when imaging.

More specifically, when the arm 106 is in a horizontal state, the articulating mechanism 104 can rotate the radiation generating unit 100 in a predetermined direction (direction B) about the longitudinal direction of the arm 106. Further, the articulating mechanism 104 can also rotate the radiation generating unit 100 in a predetermined direction (direction C) about the direction that is orthogonal to the longitudinal direction of the arm 106. Thus, the radiation generating unit 100 can be rotated about a plurality of rotational axes by the articulating mechanism 104.

The radiation generating apparatus includes a support pedestal 112 for supporting the support pillar 108. The support pedestal 112 can be detached from the support pillar 108. If performing radiation imaging at a home healthcare location, for example, the support pedestal 112 can be used by, for example, inserting under a bed. This is a type of usage suitable when utilizing the radiation generating apparatus according to the present exemplary embodiment for radiation imaging performed at a relatively low position.

The support pedestal 112 has a U shape or the like. The support pedestal 112 enables the balance of the radiation generating apparatus to be maintained even when the support pedestal 112 is not arranged directly below (the lower side in the vertical direction) the radiation generating unit 100. The radiation detection apparatus is arranged directly below (the lower side in the vertical direction) the radiation generating unit 100. Thus, the radiation detection apparatus can be arranged in an area where the support pedestal 112 is not arranged.

The support pedestal 112 may have a plurality of split leg portions. The plurality of leg portions are each in contact with the floor (or a bed). The plurality of leg portions are arranged to be placed on the floor so as to maintain the balance of the radiation generating apparatus. The support pedestal 112 can be formed in a U shape or the like by changing the shape of the plurality of leg portions. When imaging, as illustrated in FIG. 1, the support pedestal 112 has a U shape or the like. The support pedestal 112 may also include a plurality of articulated portions so that the plurality of leg portions configuring the support pedestal 112 can be folded.

Further, although an example was illustrated in which the support pedestal 112 has a plurality of leg portions, a form in which the support pedestal 112 formed with a single member is bent in a curved shape is also included in the concept of a plurality of leg portions. Further, the plurality of leg portions of the support pedestal 112 may also be configured with, for example, a collection of rod members, a collection of cylindrical members, or a collection of linear members (a mesh structure). IN other words, the plurality of leg portions of the support pedestal 112 can be applied in forms like those described above as long as they support the support mechanism (support pillar 108) supporting the radiation generating unit that emits radiation.

The support pillar 108 includes a housing portion 110 that has a space for housing the radiation generating unit 100 in the body of the support pillar 108, and an arm housing portion 114 that has a space for housing the arm 106. The arm housing portion 114 can house the articulating mechanism 104 together with the arm 106.

The housing portion 110 housing the radiation generating unit 100 and the arm housing portion 114 are formed in the support pillar 108 so as to cut into the body of the support pillar 108. Thus, the housing portion 110 and the arm housing portion 114 are groove portions having a vertical and horizontal length and a depth sufficient to allow the radiation generating unit 100 and the arm 106 to be housed. These groove portions are formed along the longitudinal direction (vertical direction) of the support pillar 108. Further, an arm hinge for allowing the arm 106 to be rotated is arranged in the groove portion. The housing portion 110 has a space for housing at least a part of the radiation generating unit 100. The housing portion 110 may have a space for housing whole of the radiation generating unit 100. The arm housing portion 114 has a space for housing at least a part of the arm 106. The housing portion 110 may have a space for housing whole of the arm 106.

The housing portion 110 housing the radiation generating unit 100 and the arm housing portion 114 are configured with a radiation shielding member such as lead that can shields the radiation emitted from the radiation generating unit 100. For example, a radiation shielding member is attached to the inner faces (groove portions) of the housing portion 110 and the arm housing portion 114.

To reduce weight, the housing portion 110 and the arm housing portion 114 may also be formed with different radiation shielding members. For example, a tungsten sheet may be attached on the inner face (groove portion) of the arm housing portion 114, and a lead panel may be attached on the inner face (groove portion) of the housing portion 110. Consequently, if the radiation generating unit 100 is housed in the housing portion 110, the leakage of radiation from the radiation generating unit 100 can be prevented by the radiation shielding member.

If the radiation generating unit 100 is housed in the housing portion 110 that is formed in the support pillar 108, as illustrated in FIG. 1, the operator rotates the radiation generating unit 100 in direction B and direction C via the articulating mechanism 104. In other words, when the operator folds the arm 106, the radiation generating unit 100 rotates the radiation generating unit 100 to be housed in the housing portion 110.

Figure 2:
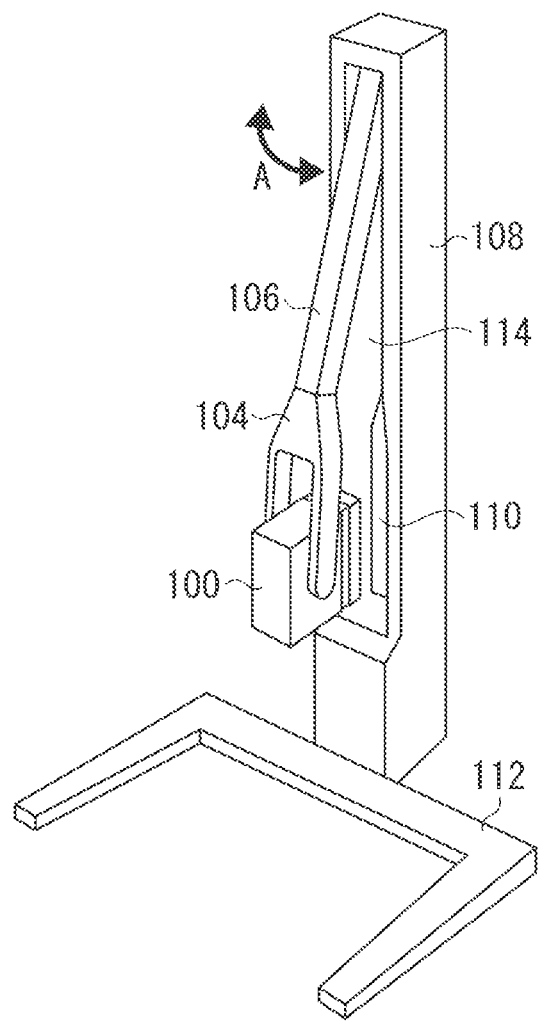
FIG. 2 illustrates an operation form of a radiation generating apparatus according to the first exemplary embodiment of the present invention.

FIG. 2 illustrates an operation form of a radiation generating apparatus. The form illustrated in FIG. 2 occurs when the operator rotates the arm 106 via the arm hinge in order to rotate the arm 106 in a predetermined direction (direction A). When the arm 106 is further rotated to the support pillar 108 side, the operator checks whether the radiation generating unit 100 has been housed in the housing portion 110. When the arm 106 is further rotated to the support pillar 108 side, if the radiation generating unit 100 is housed in the housing portion 110 (i.e., in a state in which the radiation generating unit 100 does not protrude from the housing portion 110), the operator further rotates the arm 106 to the support pillar 108 side. If the radiation generating unit 100 is not housed in the housing portion 110 (i.e., in a state in which the radiation generating unit 100 protrudes from the housing portion 110), the operator adjusts the position by rotating the radiation generating unit 100 in direction B and direction C via the articulating mechanism 104 so that the radiation generating unit 100 is housed in the housing portion 110 (i.e., in a state in which the radiation generating unit 100 does not protrude from the housing portion 110). Then, the operator rotates the arm 106 to the support pillar 108 side.

Figure 3:
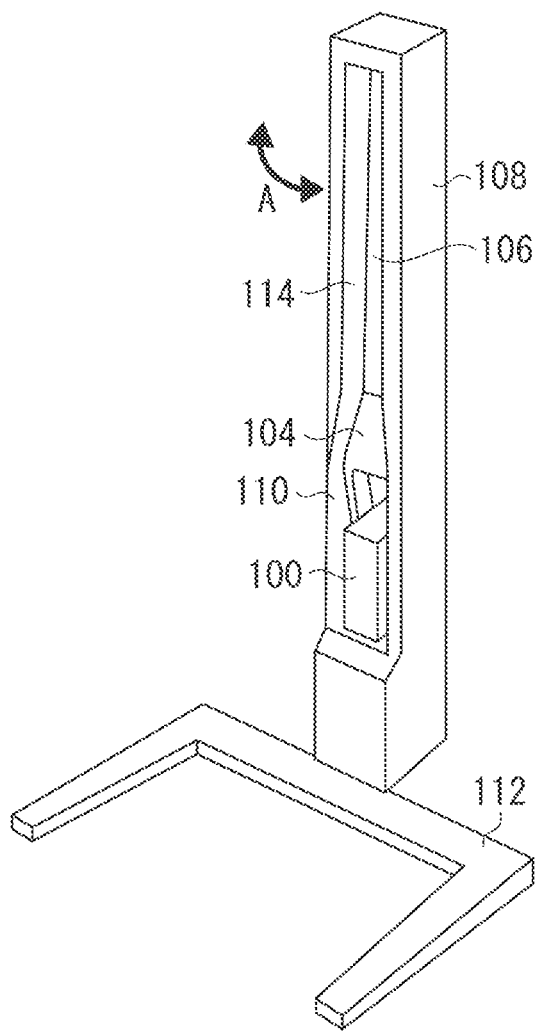
FIG. 3 illustrates a housing form of a radiation generating apparatus according to the first exemplary embodiment of the present invention.

FIG. 3 illustrates a housing form of a radiation generating apparatus. The operator folds the arm 106 so that the arm 106 is substantially parallel to the support pillar 108. In this state, the radiation generating unit 100 is arranged near the floor. At this stage, the radiation generating unit 100 is housed in the housing portion 110, and the arm 106 is housed in the arm housing portion 114. When the radiation generating unit 100 and the arm 106 have been housed, the radiation generating unit 100 and the arm 106 are integral with the support pillar 108.

The housing portion 110 of the support pillar 108 includes a lock mechanism that locks rotation of the radiation generating unit 100 when the radiation generating unit 100 is housed in the housing portion 110 of the support pillar 108. The lock mechanism is a mechanism for locking rotation of the radiation generating unit 100 when the aperture portion 102, which determines the emission direction of the radiation, is aligned with the shaft direction of the support pillar 108. More specifically, the lock mechanism locks the arm hinge portion for rotating the arm 106 in direction A and the articulating mechanism 104 for rotating the radiation generating unit 100 in direction B and direction C.

With the lock mechanism, when housing the radiation generating unit 100 in the housing portion 110, the radiation generating unit 100 is housed with the aperture portion 102 fixed facing the support pillar 108. The housing direction of the radiation generating unit 100 is the direction in which the aperture portion 102, which determines the emission direction of the radiation, is hidden from the portion facing the external air. The aperture portion 102, which determines the emission direction of the radiation, is made to face the radiation shielding member provided in the housing portion 110 of the support pillar 108. Therefore, the radiation emitted from the radiation generating unit 100 can be shielded. As a result, if the radiation generating unit 100 is housed in the housing portion 110, the operator can be protected from radiation leakage by the radiation shielding member, so that safety can be maintained.

Further, as another housing form, the lock in the direction of the aperture portion 102 may be set in the floor direction of the support pillar 108 during the period from housing of the radiation generating unit 100 until rotation of the arm 106. In this case, the aperture portion 102 of the radiation generating unit 100 always faces the floor direction when the support pillar 108 is erect, so that the aperture portion 102 can be prevented from facing the operator who is standing by the apparatus during the period from housing until rotation of the arm 106.

In addition, the support pillar 108 may have a handle (not illustrated) for the operator to grasp when carrying the radiation generating apparatus. For example, the handle may be provided near the middle of the support pillar 108. The operator can carry the radiation generating apparatus by grasping the handle and lifting it up.

A power supply unit (not illustrated) for supplying power to the radiation generating unit 100 may also be provided in the support pillar 108. More specifically, the power supply unit is provided at the lower end of the support pillar 108, and is integrated with the support pillar 108. The power supply unit is provided on the opposite side (the rear side in FIG. 1) of the side on which the radiation generating unit 100 is arranged (the front side in FIG. 1). The power supply unit is provided on a side face of the support pillar 108 so as not to be interfered with by the arm 106 or the radiation generating unit 100 when the arm 106 is folded.

Further, when the arm 106 is folded and the arm 106 has been housed with the radiation generating unit 100, the radiation generating unit 100 and the power supply unit are each arranged on the side near the floor. Since the radiation generating unit 100 and the power supply unit, which are comparatively heavy, are positioned near the floor, the operator can stably carry the radiation generating apparatus using the handle.

The support pillar 108 has a separation mechanism (not illustrated) for separating the support pillar 108 from the support pedestal 112. The operator can detach the support pillar 108 from the support pedestal 112. Therefore, the operator can carry the radiation generating apparatus by separating the support pedestal 112 from the other constituent parts (the radiation generating unit 100, the arm 106, the support pillar 108, and the power supply unit).

As illustrated in FIGS. 4A and 4B, the radiation generating apparatus other than the support pedestal 112 that is separated therefrom includes at least the radiation generating unit 100, the arm 106, the support pillar 108, and the power supply unit. When imaging, although the operator needs to move the radiation generating unit 100 according to the imaging site of the subject, the operator does not need to move the power supply unit. Therefore, as described above, the radiation generating unit 100 is arranged on the arm 106, and the power supply unit is arranged on the support pedestal 112. Thus, the radiation generating unit 100 and the power supply unit are each arranged on different constituent parts.

According to the present exemplary embodiment, the radiation generating apparatus includes the radiation generating unit 100 that generates radiation, the arm 106 that supports the radiation generating unit 100, and the support pillar 108 that supports the arm 106 to rotate the arm 106, and the support pillar 108 has a housing portion 110 that has a space for housing at least a part of the radiation generating unit 100. Further, the radiation imaging apparatus includes the radiation generating apparatus, a radiation detection apparatus configured to detect radiation that has passed through a subject, and a display device that displays an image based on the detected data.

In other words, the radiation generating apparatus includes the radiation generating unit 100 that generates radiation, the arm 106 that supports the radiation generating unit 100, and the support pillar 108 that supports the arm 106 at a predetermined height from the floor. The support pillar 108 has a hollow portion. The arm 106 can be rotated about the upper end of the support pillar 108, and be housed with the radiation generating unit 100 in the hollow portion of the support pillar 108.

Therefore, the radiation generating apparatus according to the present exemplary embodiment has an excellent accommodatability, and has excellent transportability. Thus, the operator can easily transport the radiation generating apparatus and the radiation imaging apparatus. Further, by detaching the support pedestal 112, these apparatuses can be easily transported and mounted in a vehicle. The apparatuses can be quickly ready for a radiation imaging form simply by attaching the support pedestal 112 to the support pillar 108. Further, since the aperture portion 102 of the radiation generating unit 100 is housed in the support pillar 108 that is formed with a radiation shielding member, radiation leakage can be prevented.

Further, in the present exemplary embodiment, the support pillar 108 includes, in the body of the support pillar 108, the housing portion 110 that has a space for housing the radiation generating unit 100, and the arm housing portion 114 that has a space for housing the arm 106. However, the support pillar 108 may have only the housing portion 110 that has the space for housing the radiation generating unit 100 in the body of the support pillar 108.

Next, a second exemplary embodiment will be described. FIGS. 4A and 4B illustrate an appearance of a radiation generating apparatus according to the second exemplary embodiment of the present invention. The difference from the first exemplary embodiment is that the radiation generating apparatus has a cover 200 for covering the radiation generating unit 100 housed in the housing portion 110.

FIG. 4A illustrates a state before the cover 200 is mounted on the support pillar 108, and FIG. 4B illustrates a state after the cover 200 has been mounted on the support pillar 108. The cover 200, which is configured so as to be engageable with the support pillar 108, can cover the radiation generating unit 100 housed in the housing portion 110. The shape of the cover 200 is defined so that the radiation generating apparatus attached to the cover 200 on the support pillar 108 is substantially a quadrangular prism.

The cover 200 is configured using a radiation shielding member such as lead that can shield the radiation emitted from the radiation generating unit 100. For example, a radiation shielding member is attached to the inner face (radiation generating unit 100 side) of the cover 200.

The operator houses the radiation generating unit 100 in the housing portion 110 and covers the radiation generating unit 100 with the cover 200. Consequently, the operator can be better protected from radiation leaks from the radiation generating unit 100 by the radiation shielding member of the support pillar 108 and the radiation shielding member of the cover 200.

More specifically, as illustrated in FIG. 4A, the cover 200 has a plurality of convex portions 202 and 204. Further, the support pillar 108 has a plurality of concave portions 150, 152, 154, and 156 at positions corresponding to the plurality of convex portions 202 and 204. The convex portion 202 provided in the cover 200 is inserted into the concave portions 150 and 152 provided in the support pillar 108. The convex portion 204 provided in the cover 200 is inserted into the concave portions 154 and 156 provided in the support pillar 108. The plurality of convex portions 202 and 204 are inserted in the same manner in the concave portions 150, 152, 154, and 156, so that the cover 200 is engaged with the support pillar 108. This enables the cover 200 to be mounted on the support pillar 108.

In the above description, although the cover 200 covering the support pillar 108 using a plurality of convex portions 202 and 204 and concave portions 150, 152, 154, and 156 is described, the cover 200 may be changed, as long as the cover 200 covers the radiation generating unit 100 housed in the housing portion 110. For example, a configuration in which a groove is provided in the longitudinal direction of the support pillar 108, and the cover 200 is attached to the support pillar 108 by sliding the cover 200 covering the radiation generating unit 100 housed in the housing portion 110 along the groove provided in the support pillar 108, may be employed. Further, the cover 200 covering the radiation generating unit 100 housed in the housing portion 110 may be arranged on the support pillar 108 using a hinge.

As illustrated in FIG. 4B, when the cover 200 is attached to the support pillar 108, the radiation generating apparatus is substantially a quadrangular prism, which is suitable for transporting the radiation generating apparatus. Therefore, the operator can transport the radiation generating apparatus easily and safely.

Further, when the operator is transporting the radiation generating apparatus, a configuration with better protection can be obtained by housing the support pillar 108 in which the arm 106 and the radiation generating unit 100 are housed in a case (not illustrated). This case (not illustrated) may be a hard case or a soft case.

Figure 5:
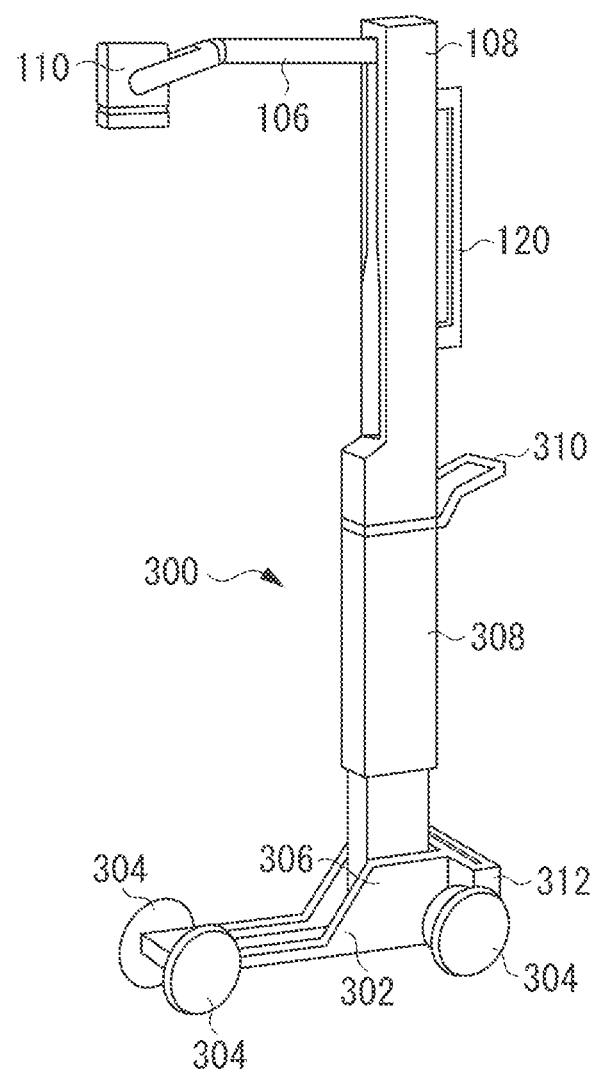
FIG. 5 illustrates an appearance of a radiation generating apparatus according to a third exemplary embodiment of the present invention.

Next, a third embodiment will be described. FIG. 5 illustrates an appearance of a radiation generating apparatus according to a third exemplary embodiment of the present invention. The difference from the first and second exemplary embodiments is that the radiation generating apparatus has a movable portion that can move the radiation generating apparatus along the floor.

FIG. 5 illustrates a case in which, in the radiation generating apparatus according to the present invention, the support pedestal 112 illustrated in FIG. 1 has been detached, and a movable portion 300 for moving along the floor is attached. Description of the parts including the radiation generating unit 100 and the support pillar 108 will be omitted here, as it is similar to that in FIG. 1. A form in which the radiation generating apparatus is mounted on the movable portion 300 is suitable for imaging by moving the radiation generating apparatus to a hospital room. The radiation generating unit 100 can be brought closer to the affected area of the subject by placing the anterior portion of the movable portion 300 beneath the bed.

FIG. 5 illustrates a form of a support pedestal that allows the radiation generating apparatus to move. The support pedestal and the radiation generating unit 100 configures the movable portion 300 capable of moving along the floor. More specifically, the movable portion 300 has wheels 304 that roll along the floor. The wheels 304 are a plurality of tires or casters that are always touching the floor. By rolling the wheels 304, the movable portion 300 (the radiation generating apparatus) can be moved in forward and backward directions.

The movable portion 300 has a support portion 308 for supporting the support pillar 108. While imaging, the support portion 308 is erected in the vertical direction. The support portion 308, which has a predetermined length, includes an extension/contraction mechanism for extending/contracting the support portion 308 in a longitudinal direction. The support portion 308 may also have a lock portion (not illustrated) for fixing the extension/contraction of the extension/contraction mechanism. The support portion 308 can be extended/contracted by releasing the fix on extension/contraction by the lock portion.

Further, the movable portion 300 has a rotation mechanism 306 that rotates the support portion 308. The support portion 308 can be tilted forward by the rotation mechanism 306. By rotating the support portion 308, the support portion 308 can be made parallel to the floor. By housing the support portion 308, the movable portion 300 can be made compact.

A support member 302 is a constituent part that supports the radiation generating apparatus. As illustrated in FIG. 5, the constituent parts in the radiation generating apparatus that are in contact with the floor are the plurality of wheels 304. The support member 302 of the movable portion 300 rotatably supports the plurality of wheels 304. Further, the radiation generating apparatus is supported by the wheels 304 and the support member 302 of the movable portion 300. The area in contact with the floor of the radiation generating apparatus can be widened by the support member 302. Therefore, for example, the balance of the radiation generating apparatus can be maintained by the support member 302 even when the radiation generating unit 100 is positioned at an imaging site of the subject.

The support portion 308 has a coupling portion (not illustrated) for detachably coupling thereof with the support pillar 108. More specifically, the upper end of the support portion 308 has a coupling portion that couples with the support pillar 108. The coupling portion is a member that protrudes upwards from the upper end. The support pillar 108 is hollow. As illustrated in the FIG. 5, the movable portion 300 couples with the support pillar 108 by fitting the upwards-protruding coupling portion inside the support pillar 108.

A handle 310 for the operator to grasp is included on the support portion 308. This handle 310 is used as a position to hold when moving or transporting. The handle 310 can also be used as a tray on which a laptop computer or a tablet computer can be mounted for controlling radiation irradiation by the radiation generating unit 100 during imaging.

The movable portion 300 may include a holder 312 for housing the radiation detection apparatus. The radiation detection apparatus is a flat panel detector. More specifically, the holder 312 housing the radiation detection apparatus is arranged on the support member 302. The holder 312 is arranged on the opposite side (the rear side in FIG. 5) of the side on which the radiation generating unit 100 is arranged (the front side in FIG. 5). The holder 312 is arranged on a side face of the support member 302 so as not to be interfered with by the arm 106 or the radiation generating unit 100 when the arm 106 is folded. Further, the radiation detection apparatus includes relatively heavy constituent parts. The balance of the radiation generating apparatus can be stabilized by housing the radiation generating apparatus in the holder 312 arranged on the end of the support member 302 (the side close to the floor).

The support pillar 108 has a handle 120 for the operator to grasp when transporting the radiation generating apparatus. By grasping the handle 120 and lifting it up, the operator can separate the radiation generating apparatus from the movable portion 300, and carry the radiation generating apparatus around.

According to the present exemplary embodiment, the radiation generating apparatus can be moved with the radiation generating unit 100 and the support pillar 108 housed in the support pillar 108. Therefore, the risk of the radiation generating unit 100 and the arm 106 coming into contact with obstructions when moving can be reduced. Further, even at the imaging location, the radiation generating apparatus can be quickly readied for a radiation imaging mode simply by raising the radiation generating unit 100 and the arm 106 from the support pillar 108.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-189448 filed Sep. 12, 2013, which is hereby incorporated by reference herein in its entirety.

What is claimed is:

1. A radiation generating apparatus comprising:
   a radiation generating unit configured to generate radiation;
   an arm configured to support the radiation generating unit; and
   a support pillar configured to support the arm and rotate the arm,
   wherein the support pillar comprises a housing portion that has a space for housing at least a part of the radiation generating unit.

2. The radiation generating apparatus according to claim 1, wherein the support pillar comprises an arm housing portion that has a space for housing at least a part of the arm.

3. The radiation generating apparatus according to claim 1, wherein the arm is configured to rotate around an upper end of the support pillar.

4. The radiation generating apparatus according to claim 1, wherein the support pillar comprises a radiation shielding member.

5. The radiation generating apparatus according to claim 4, wherein the radiation shielding member is any one of a lead panel and a tungsten sheet.

6. The radiation generating apparatus according to claim 1, wherein the housing portion comprises a radiation shielding member covering an inner face of the housing portion.

7. The radiation generating apparatus according to claim 1, wherein the radiation generating unit comprises an aperture portion, and
   wherein, in a state in which the aperture portion of the radiation generating unit is facing the support pillar, the radiation generating unit is housed in the housing portion.

8. The radiation generating apparatus according to claim 1, wherein the radiation generating unit comprises an aperture portion, and
   wherein, in a state in which the aperture portion of the radiation generating unit is facing in a floor direction, the radiation generating unit is housed in the housing portion.

9. The radiation generating apparatus according to claim 1, further comprising a support pedestal configured to support the support pillar, wherein the support pedestal is detachable from the support pillar.

10. The radiation generating apparatus according to claim 1, further comprising a lock mechanism configured to lock rotation of the radiation generating unit when the radiation generating unit is housed in the housing portion.

11. The radiation generating apparatus according to claim 1, further comprising a cover configured to cover the radiation generating unit housed in the housing portion.

12. The radiation generating apparatus according to claim 1, further comprising a movable portion configured to move along a floor with the radiation generating unit.

* * * * *